(12) United States Patent
Jelle et al.

(10) Patent No.: US 10,806,904 B2
(45) Date of Patent: Oct. 20, 2020

(54) TWO-PART INSERTION TOOL AND METHODS

(71) Applicant: Surmodics, Inc., Eden Prairie, MN (US)

(72) Inventors: Bruce M. Jelle, Eden Prairie, MN (US); Joram Slager, St. Louis Park, MN (US); Joseph Schmidt McGonigle, Minneapolis, MN (US); Nathan A. Lockwood, Minneapolis, MN (US)

(73) Assignee: Surmodics, Inc., Eden Prairie, MN (US)

( * ) Notice: Subject to any disclaimer, the term of this patent is extended or adjusted under 35 U.S.C. 154(b) by 678 days.

(21) Appl. No.: 15/467,554

(22) Filed: Mar. 23, 2017

(65) Prior Publication Data

US 2017/0281907 A1 Oct. 5, 2017

Related U.S. Application Data

(60) Provisional application No. 62/316,153, filed on Mar. 31, 2016.

(51) Int. Cl.
*A61M 25/06* (2006.01)
*A61M 25/00* (2006.01)
*A61M 39/06* (2006.01)

(52) U.S. Cl.
CPC .... *A61M 25/0662* (2013.01); *A61M 25/0023* (2013.01); *A61M 25/0045* (2013.01);
(Continued)

(58) Field of Classification Search
CPC .......... A61M 25/0662; A61M 25/0097; A61M 25/0668; A61M 2025/0681; A61M 2025/0675

See application file for complete search history.

(56) References Cited

U.S. PATENT DOCUMENTS 4,973,993 A 11/1990 Allen
5,414,075 A 5/1995 Swan et al.
(Continued)

FOREIGN PATENT DOCUMENTS

WO 2017172609 10/2017

OTHER PUBLICATIONS

"International Search Report and Written Opinion," for PCT Application No. PCT/US2017/024289 dated Jul. 3, 2017 (32 pages).
(Continued)

*Primary Examiner* — Jenna Zhang
(74) *Attorney, Agent, or Firm* — Pauly, DeVries Smith & Deffner LLC

(57) ABSTRACT

Embodiments herein include an insertion tool for inserting a medical device into another medical device, such as a hemostasis sealing valve, and related methods. In an embodiment, an insertion tool includes a guide sheath and a protection tube. The guide sheath can include a flared proximal end. The guide sheath can further include a central lumen. The guide sheath can further include a locking notch disposed on the inner surface between the proximal end and the distal end. The protection tube can include a flared proximal end. A portion of the protection tube can be situated within the central lumen of the guide sheath. The flared proximal end of the protection tube can be sized to fit within the locking notch and can have an outer diameter larger than portions of the inner surface immediately adjacent to the locking notch. Other embodiments are also included herein.

21 Claims, 8 Drawing Sheets

(52) U.S. Cl.
CPC ..... *A61M 25/0097* (2013.01); *A61M 25/0668* (2013.01); *A61M 39/06* (2013.01); *A61M 2025/006* (2013.01); *A61M 2025/0024* (2013.01); *A61M 2025/0046* (2013.01); *A61M 2025/0047* (2013.01); *A61M 2025/0681* (2013.01); *A61M 2025/0687* (2013.01); *A61M 2039/064* (2013.01); *A61M 2039/0666* (2013.01); *A61M 2207/00* (2013.01)

(56) References Cited

U.S. PATENT DOCUMENTS

| | | | |
|---|---|---|---|
| 5,637,460 A | 6/1997 | Swan et al. | |
| 5,714,360 A | 2/1998 | Swan et al. | |
| 5,858,653 A | 1/1999 | Duran et al. | |
| 5,879,333 A * | 3/1999 | Smith | A61M 25/0014 604/164.04 |
| 6,007,833 A | 12/1999 | Chudzik et al. | |
| 6,077,698 A | 6/2000 | Swan et al. | |
| 6,278,018 B1 | 8/2001 | Swan | |
| 6,465,178 B2 | 10/2002 | Chappa et al. | |
| 6,514,734 B1 | 2/2003 | Clapper et al. | |
| 6,603,040 B1 | 8/2003 | Swan | |
| 6,762,019 B2 | 7/2004 | Swan et al. | |
| 7,138,541 B2 | 11/2006 | Swan | |
| 7,309,593 B2 | 12/2007 | Ofstead et al. | |
| 7,348,055 B2 | 3/2008 | Chappa et al. | |
| 7,736,689 B2 | 6/2010 | Chappa et al. | |
| 7,744,571 B2 * | 6/2010 | Fisher | A61M 39/0606 604/167.04 |
| 7,772,393 B2 | 8/2010 | Guire et al. | |
| 7,807,750 B2 | 10/2010 | Taton et al. | |
| 8,039,524 B2 | 10/2011 | Chappa et al. | |
| 8,487,137 B2 | 7/2013 | Guire et al. | |
| 8,809,411 B2 | 8/2014 | Rooijmans | |
| 8,889,760 B2 | 11/2014 | Kurdyumov et al. | |
| 2004/0059296 A1 * | 3/2004 | Godfrey | A61M 25/0668 604/164.05 |
| 2005/0090890 A1 * | 4/2005 | Wu | A61F 2/95 623/1.11 |
| 2007/0032882 A1 | 2/2007 | Lodhi et al. | |
| 2008/0262430 A1 * | 10/2008 | Anderson | A61B 17/3415 604/164.1 |
| 2009/0105652 A1 * | 4/2009 | Beal | A61M 25/0668 604/164.03 |
| 2009/0221961 A1 * | 9/2009 | Tal | A61M 25/0606 604/103.06 |
| 2010/0198168 A1 | 8/2010 | Rooijmans | |
| 2010/0274012 A1 | 10/2010 | Guire et al. | |
| 2011/0144373 A1 | 6/2011 | Swan et al. | |
| 2012/0148852 A1 | 6/2012 | Jelle et al. | |
| 2012/0149934 A1 | 6/2012 | Kurdyumov | |
| 2013/0143056 A1 | 6/2013 | Swan et al. | |
| 2013/0150793 A1 * | 6/2013 | Beissel | A61M 25/0105 604/171 |
| 2013/0302529 A1 | 11/2013 | Kurdyumov | |
| 2014/0237798 A1 * | 8/2014 | Cude | A61M 25/0662 29/428 |
| 2015/0088072 A1 * | 3/2015 | Voss | A61M 25/0009 604/164.01 |

OTHER PUBLICATIONS

"International Preliminary Report on Patentability," for PCT Application No. PCT/US2017/024289 dated Oct. 11, 2018 (9 pages).

"Response to Communication Pursuant to Rules 161(1) and 162 EPC," for European Patent Application No. 17715889.6 filed May 2, 2019 (22 pages).

* cited by examiner

TWO-PART INSERTION TOOL AND METHODS

This application claims the benefit of U.S. Provisional Application No. 62/316,153, filed Mar. 31, 2016, the contents of which are herein incorporated by reference.

FIELD

Embodiments herein relate to an insertion tool for inserting a medical device into another medical device, such as a hemostasis sealing valve, and related methods. More specifically, embodiments herein relate to a two-part insertion tool for inserting a medical device into another medical device.

BACKGROUND

Many modern medical techniques involve introducing various pieces of equipment, percutaneously, into a patient and advancing such equipment to a site to be treated. These procedures can involve both initial access and guiding of a guide wire through the vasculature as well as later steps that may require different devices. As such, there can be a need to change equipment during a procedure.

Prevention of extracorporeal blood flow while changing delivery devices during a procedure to insert a main prosthesis or other device can be accomplished through the use of a hemostasis valve. However, it is not always easy to introduce equipment into such hemostasis valves. Similarly, it is not always easy to introduce equipment into other types of devices that sit near the site of access through the skin.

SUMMARY

Embodiments herein include an insertion tool for inserting a medical device into another medical device, such as a hemostasis sealing valve, and related methods. In an embodiment, an insertion tool includes a guide sheath and a protection tube. The guide sheath can include a proximal end and a distal end, the proximal end being flared. The guide sheath can further include an inner surface defining a central lumen. The guide sheath can further include a locking notch disposed on the inner surface between the proximal end and the distal end. The protection tube can include a proximal end and a distal end, the proximal ended being flared. A portion of the protection tube can be situated within the central lumen of the guide sheath. The flared proximal end of the protection tube can be sized to fit within the locking notch and can have an outer diameter larger than portions of the inner surface immediately adjacent to the locking notch.

In an embodiment, an insertion tool includes a guide sheath having an outer diameter, an inner diameter, a proximal end and a distal end, the proximal end being flared. The insertion tool also includes a protection tube having an outer diameter, an inner diameter, a flared proximal end and a tapered distal end. The protection tube outer diameter can be less than the guide sheath inner diameter and a portion of the protection tube can be situated within the guide sheath. The flared proximal end of the protection tube can be sized to fit a locking notch located between the proximal end of the guide sheath and the distal end of the guide sheath.

In an embodiment, a method for inserting a medical device into a second medical device, such as a hemostasis sealing valve, is included. The method can include aligning an insertion tool with a hemostasis sealing valve. The insertion tool can include a guide sheath and a protection tube. The guide sheath can include a proximal end and a distal end, the proximal end being flared. The guide sheath can further include an inner surface defining a central lumen. The guide sheath can further include a locking notch disposed on the inner surface between the proximal end and the distal end. The protection tube can include a proximal end and a distal end, the proximal ended being flared. A portion of the protection tube can be situated within the central lumen of the guide sheath. The flared proximal end of the protection tube can be sized to fit within the locking notch and can have an outer diameter larger than portions of the inner surface immediately adjacent to the locking notch. The method can further include inserting the distal end of the protection tube into the hemostasis sealing valve. The method can further include inserting the medical device through the central lumen of the guide sheath into the protection tube and through the hemostasis sealing valve.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
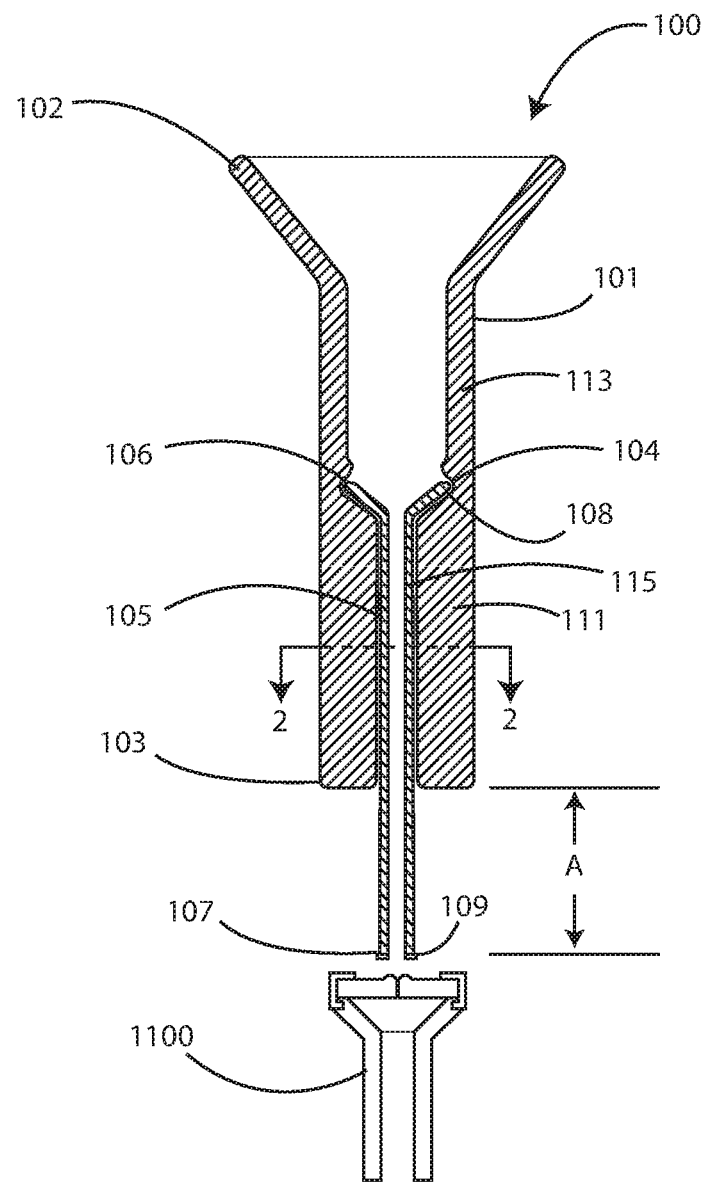
FIG. 1 is a schematic view of an exemplary insertion tool device including a guide sheath and a protection tube in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Included herein are insertion tools for medical devices that are introduced into the vasculature. The insertion tools can be used for packaging and protecting an implantable or insertable medical device during storage and deployment. The insertion tools can be used to protect and facilitate the insertion of medical devices such as balloon catheters, stents, filters, shunts and the like. The insertion tool may facilitate guidewire insertion into a catheter lumen, protect the surface of a balloon member of a balloon catheter or stent during guide wire loading, provide the insertable or implantable medical device in a desired configuration prior to insertion, protect the device from contamination, and facilitate insertion into or through an access device, including, but not limited to, a hemostasis valve.

The insertion tool can be a part of a kit or system used for a medical procedure, which are also embodiments of the invention. For example, the kit can include one or more of the following components: one or more delivery catheters, a balloon treatment device, an inflation catheter, a stent, a guidewire, or combinations thereof.

In one embodiment, the invention provides an insertion tool for facilitating the entry of a medical device such as a balloon catheter into the body. The insertion tool can be a two-piece construct including (i) a guide sheath and (ii) a protection tube. The guide sheath can be flared on the proximal end tapering to an opening on the distal end. Additionally the guide sheath can have a locking notch located between the proximal end and the distal end. The outer diameter of the protection tube can be sized to fit within the inner diameter of the guide sheath. The proximal end of the protection tube can be flared. In some embodiments the flared end of the protection tube can be sized to fit in the locking notch of the guide sheath, thus securing the protection tube within the inner circumference of the guide sheath and preventing movement between the guide sheath and protection tube. Typically, the guide sheath of the two-piece construct can have a thicker wall dimension than the protection tube. The thicker wall aids the medical practitioner in handling the device to avoid crushing the protection tube against the medical device (for example, but not limited to a drug-containing balloon) and damaging the medical device being inserted through the insertion tool. The two-piece construct can also allow for the guide sheath and the protection tube to be made from materials that may otherwise be incompatible with each other or difficult to process economically.

The two piece construct described above can be manufactured and provided to the practitioner as a single unit whereby the protection sheath is already provided in the locking notch of the guide sheath. Other manufacturing embodiments include providing the protection tube separate from the guide sheath to the medical practitioner such that the medical practitioner has more choices as to the protection tube best suited for the particular use and valve being passed by the medical device. In that embodiment, the medical practitioner can chose the appropriate protection tube and guide sheath, locking the protection tube into the chosen guide sheath.

In another embodiment, the invention provides an insertion tool for facilitating the entry of a medical device, such as a balloon catheter, into the body, the tool including a tubular member comprising a wall having an inner surface, and proximal and distal ends and a length between the ends defining a first axis. The inner surface of the wall comprises a plurality of ridges running parallel to the first axis and about the circumference of the inner wall. The ridges define areas of the wall having a first thickness, and between the ridges areas of the wall having a second thickness wherein the first thickness is greater than the second thickness. Material of the tubular member is configured to fracture along the length of the wall between the ridges when outward forces are applied to each half the tubular member. Also at the proximal end of the tubular member is a first notch that is adjacent to the proximal end of a first area of the of the tubular member that is between a first set of two ridges, and a second notch that is adjacent to the proximal end of a second area of the of the tubular member that is between a second set of two ridges. The tool also includes first and second separation assist members or tabs connected to the proximal end of the tubular member and opposite one another on the tubular member and between the first and second notches.

Embodiments of the invention also provide methods for delivering a medical device into a patient's body using the insertion tool embodiments of the invention. The method includes steps of (a) providing an insertion tool loaded with an implantable or insertable medical device such as a balloon catheter, and (b) moving, directly or indirectly, the insertable or implantable medical device from the insertion tool into the patient's body. In some embodiments the medical device can be moved past a hemostasis sealing valve using the introducer tools as described herein without damage to the surface of the medical device from handling by the medical practitioner or contact with the surface of the hemostasis sealing valve.

In another embodiment, the invention also provides another method for introducing a balloon catheter into the body. The method comprises use of a hemostatic valve and a balloon catheter insertion tool. In the method a hemostatic valve comprising proximal and distal openings is engaged with an artery. An insertion tool is provided, the tool comprising a tubular member comprising outer and inner surfaces; a distal end comprising an opening and defining inner and outer diameters, a proximal end comprising an opening and having inner and outer surfaces defining inner and outer diameters, wherein between the proximal and distal ends the outer surface of the tubular member is sized to fit within a portion of the hemostatic valve; a length between the proximal and distal ends that is greater that a length between two openings of a hemostatic valve; a flange arranged about the outer diameter of the proximal end; wherein the inner diameter of the distal end is smaller than the inner diameter of the proximal end, thereby providing a tapered configuration to the tubular member. The distal end of the insertion tool is moved through the first and second openings of the hemostatic valve so the proximal opening of the hemostatic valve is tightened around the outer surface of the insertion tool. A balloon portion of a balloon catheter is moved through the insertion tool and into the artery.

Referring now to examples shown in the figures, FIG. 1 illustrates an exemplary insertion tool 100 constructed of two pieces: a guide sheath 101 and a protection tube 105 inserted into the guide sheath 101, the protection tube 105 extending from the distal end of the guide sheath 101. The guide sheath 101 has a proximal end 102 and a distal end 103. In some embodiments, the proximal end 102 of the guide sheath 101 is flared. Exemplary values for the outside average diameter of the proximal end 102 of the guide sheath can be in the range from 0.75 mm to 12 mm. The flared end can aid the medical practitioner in threading a medical device through the insertion tool 100. Between the proximal end 102 of the guide sheath 101 and the distal end 103 of the guide sheath 101 a locking notch 104 can be located on the interior surface of the guide sheath 101.

The protection tube 105 has a distal end 107 and a proximal end 106. The proximal end 106 of the protection tube can have a locking flare 108. The locking flare 108 at the proximal end 106 of the protection tube 105 serves to engage with the locking notch 104 of the guide sheath 101. Exemplary values for average diameters of protection tube 105 can be in the range from 0.33 mm to 6.67 mm (1-20 Fr). The engagement of the locking flare 108 with the locking notch can prevent unwanted movement of the protection tube 105 with respect to the guide sheath 101. This provides for stability of the protection tube 105 upon introduction of the insertion tool 100 into and through a hemostasis valve 1100.

When the locking flare 108 is engaged with the locking notch 104, the distance (A) between the distal end 107 of the protection tube 105 and the distal end of the guide sheath 101 can be from about 2 to about 10 mm. In some embodiments, a flange 109 can be disposed on the distal end 107 of the protection tube 105. In some embodiments, the protection tube 105 has a wall thickness 115 that is less than the wall thickness 111 of the guide sheath 101 at a vertically aligned point when the locking flare 108 is engaged with the locking notch 104. Exemplary values for wall thickness 111 can be in the range from 0.010 inches to 0.030 inches. In some embodiments, the wall thickness of the guide sheath 101 is consistent throughout the length of the guide sheath 101. However, in other embodiments, the wall thickness of the guide sheath 101 can vary. For example, in some embodiments, the wall thickness 111 of the guide sheath 101 at a point below the locking notch 104 can be greater than the wall thickness 113 of the guide sheath 101 at a point above the locking notch 104. Exemplary values for wall thickness 113 can be in the range from 0.5 mm to 2.5 mm.

Sizing for various elements of the insertion tool 100 can be appropriately chosen to fit hemostasis valve 1100. Additionally, sizing of various elements, for example, but not limited to, the guide sheath 101, can be chosen to produce improved handling of insertion tool 100 by the medical professional. Materials for external surfaces of the guide sheath 101 can also be altered for increased slip resistance and handling by the medical professional.

Figure 2:
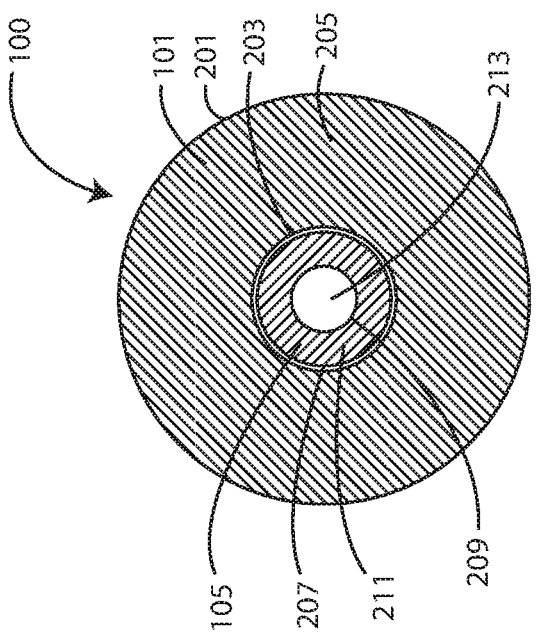
FIG. 2 is a schematic cross-sectional view of the insertion tool as taken along line 2-2 of FIG. 1.

Referring now to FIG. 2, a schematic cross-sectional view is shown of an insertion tool 100 as taken along line 2-2 of FIG. 1. The insertion tool 100 includes a guide sheath 101 and a protection tube 105. The guide sheath 101 can include an outer surface 201 (or abluminal surface), an inner surface 203 (or luminal surface), and can include substrate 205 formed of a material. Similarly, the protection tube 105 can include an outer surface 207 (or abluminal surface), an inner surface 209 (or luminal surface), a lumen 213, and can include a substrate 211 formed of a material.

The materials of the guide sheath 101 and the protection tube 105 can be the same or they can be different. In some embodiments, the substrate 205 of the guide sheath can include polyamide, polyimide, polyether block amide (PE-BAX), polyether ether ketone (PEEK), high density polyethylene (HDPE), polyethylene, polyurethane, or polyethylene vinyl acetate, or combinations thereof.

In some embodiments, the substrate 211 of the protection tube 105 can include polyamide, polyimide, polyether block amide (PEBAX), polyether ether ketone (PEEK), high density polyethylene (HDPE), polyethylene, polyurethane, or polyethylene vinyl acetate, or combinations thereof.

Figure 3:
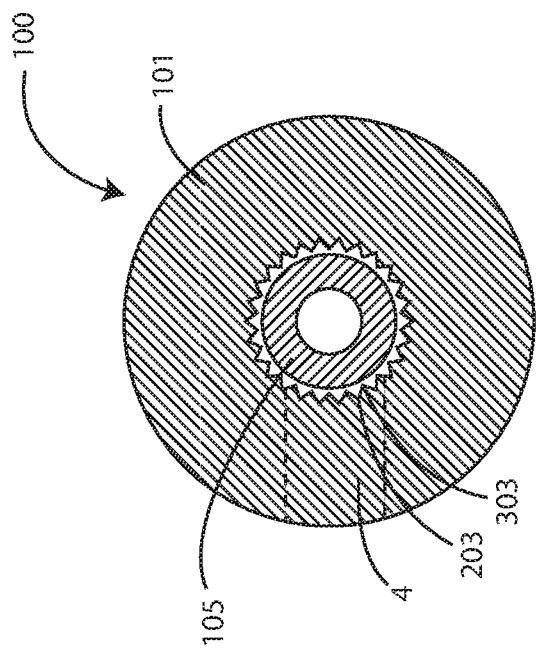
FIG. 3 is a schematic cross-sectional view of an alternative embodiment of the insertion tool as taken along line 2-2 of FIG. 1.

In some embodiments, one or more surfaces of the guide sheath 101 and/or protection tube 105 can include features to reduce the friction of items passing through the lumen thereof. For example, in some embodiments, a luminal surface can include ridges in order to minimize the surface area that comes in contact with anything passing through the lumen of the guide sheath 101 and/or protection tube 105. Referring now to FIG. 3 is a schematic cross-sectional view is shown of an alternative embodiment of the insertion tool 100 as taken along line 2-2 of FIG. 1. The insertion tool 100 includes the guide sheath 101 and the protection tube 105 disposed therein. The inner surface 203 (or luminal surface) can include a plurality of ridges 303.

Figure 4:
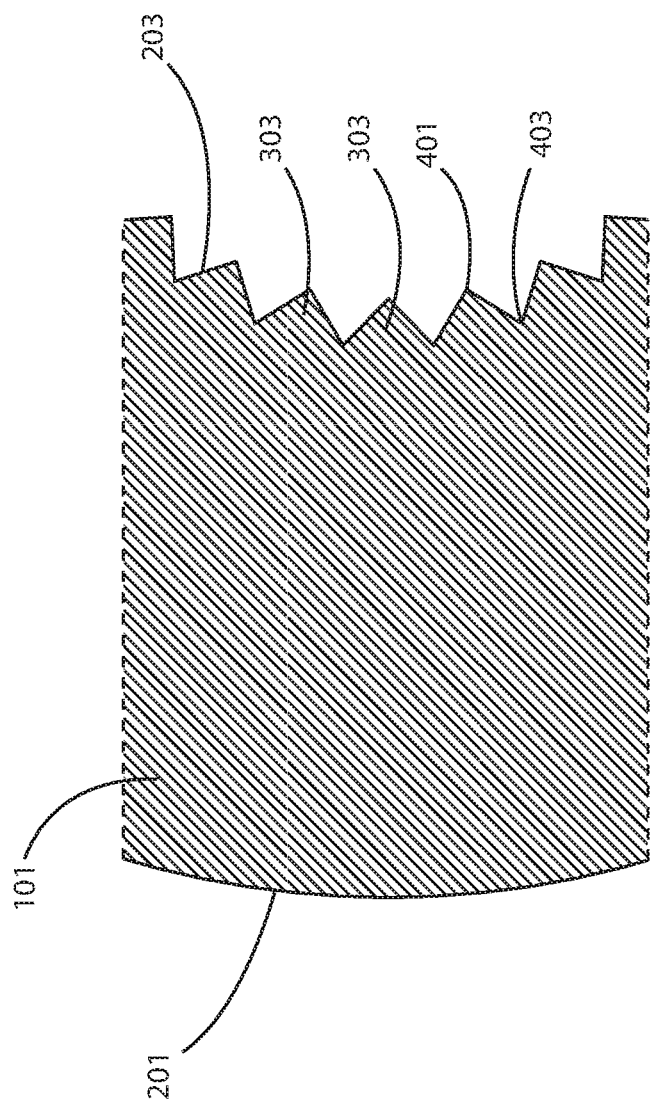
FIG. 4 is a schematic cross-sectional view of a portion of the guide sheath shown in FIG. 3.

FIG. 4 is a schematic cross-sectional view of a portion (4) of the guide sheath 101 shown in FIG. 3. The guide sheath 101 includes an outer surface 201 and an inner surface 203. The inner surface can include a plurality of ridges 303. The ridges 303 can include a series of peaks 401 and valleys 403. The ridges 303 can have various pitches. The distance between adjoining peaks 401 and valleys 403 can also vary.

Figure 5:
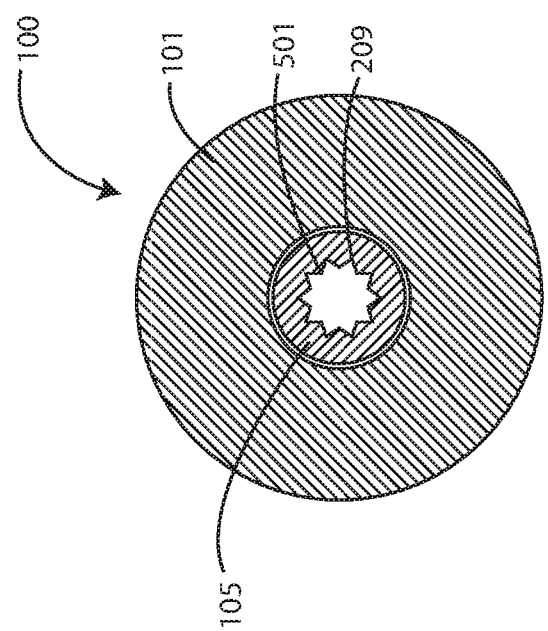
FIG. 5 is a schematic cross-sectional view of an alternative embodiment of the insertion tool as taken along line 2-2 of FIG. 1.

In some embodiments, the inner surface of the protection tube 105 can include ridges. Referring now to FIG. 5, a schematic cross-sectional view of an alternative embodiment of the insertion tool 100 is shown as taken along line 2-2 of FIG. 1. The insertion tool 100 includes a guide sheath 101 and a protection tube 105 disposed therein. The protection tube 105 includes an inner surface 209 and a plurality of ridges 501 disposed on the inner surface 209.

Figure 6:
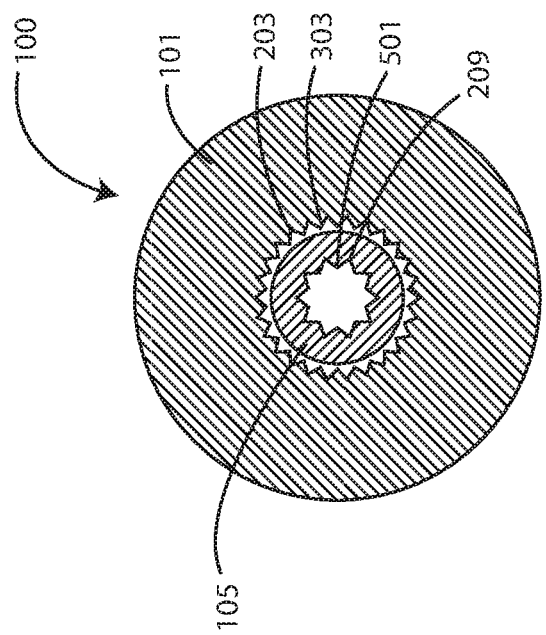
FIG. 6 is a schematic cross-sectional view of an alternative embodiment of the insertion tool as taken along line 2-2 of FIG. 1.

In some embodiments, the inner surfaces of both the protection tube 105 and the guide sheath 101 can include ridges. Referring now to FIG. 6, a schematic cross-sectional view of an alternative embodiment of the insertion tool 100 is shown as taken along line 2-2 of FIG. 1. The insertion tool 100 includes a guide sheath 101 and a protection tube 105 disposed therein. The guide sheath 101 includes an inner surface 203. The inner surface can include a plurality of ridges 303. The protection tube 105 includes an inner surface 209 and a plurality of ridges 501 disposed on the inner surface 209.

Figure 7:
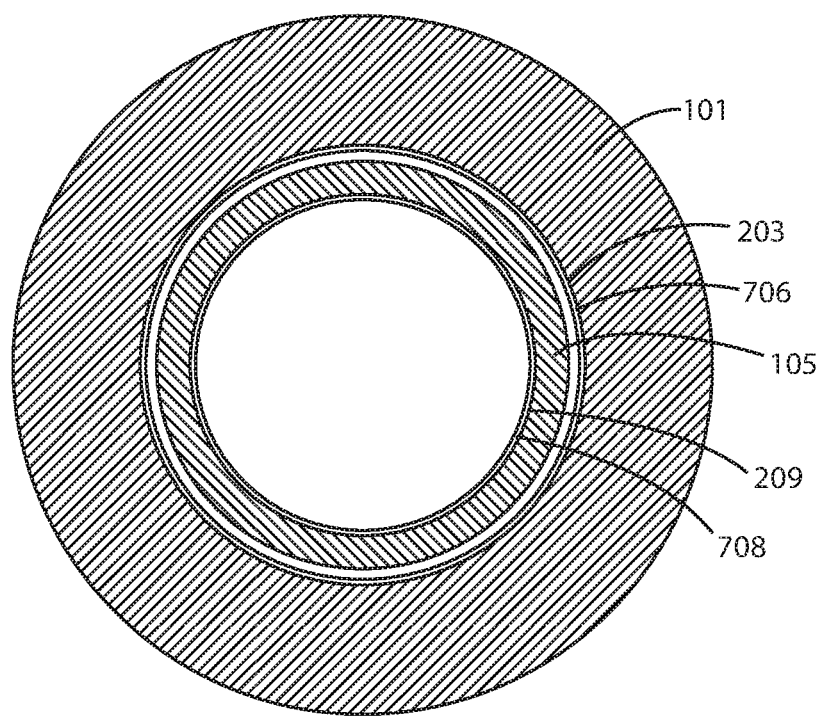
FIG. 7 is a schematic cross-sectional view of a portion of an insertion tool in accordance with various embodiments herein.

It will be appreciated that various coatings can be disposed onto the surfaces of the insertion tool 100, such as on the surfaces of the guide sheath 101 and the protection tube 105. Referring now to FIG. 7, a schematic cross-sectional view of a portion of an insertion tool 100 is shown in accordance with various embodiments herein. The insertion tool 100 can include a guide sheath 101 having an inner surface 203. In some embodiments, a coating 706 can be disposed on the inner surface 203. The coating 706 can provide various properties. For example, the coating 706 can be a lubricious coating, including, but not limited to, a hydrophilic coating. Various exemplary coating materials are described in greater detail below. The insertion tool 100 can also include a protection tube 105 having an inner surface 209. In some embodiments, a coating 708 can be disposed on the inner surface 209. The coating 708 can provide various properties. For example, the coating 708 can be a lubricious coating, including, but not limited to, a hydrophilic coating. Exemplary coating materials are described in greater detail below.

In some cases it can be desirable to be able to remove portions of the insertion tool (such as the guide sheath and/or the protection tube) after an instrument such as a guide wire has been passed there through. To facilitate removal of portions of the insertion tool, breakage lines, scoring lines, or weakened lines can be included so as to allow relatively easy breakage or cracking of the guide sheath and/or protection tube into discrete portions that will no longer surround an instrument such as a guidewire and therefore can be easily removed.

Figure 8:
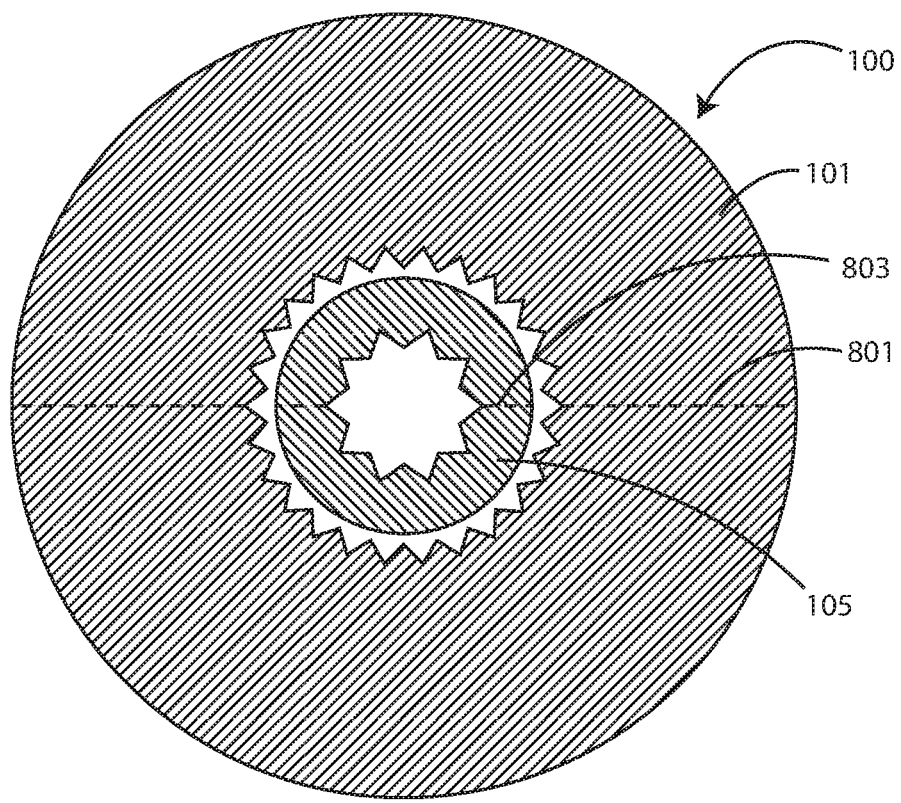
FIG. 8 is a schematic cross-sectional view of a portion of an insertion tool in accordance with various embodiments herein.

Referring now to FIG. 8, a schematic cross-sectional view of a portion of an insertion tool 100 is shown in accordance with various embodiments herein. The insertion tool 100 includes a guide sheath 101 and a protection tube 105 disposed therein. The guide sheath 101 includes a breakage line 801 to facilitate breaking the guide sheath 101 into discrete portions. The protection tube 105 includes a breakage line 803 to facilitate breaking the protection tube 105 into discrete portions. The breakage line 803 can be weakened compared to other parts of the guide sheath or protection tube using scoring, partial cuts, small bubbles, or any other technique of weakening the material at that point.

Figure 9:
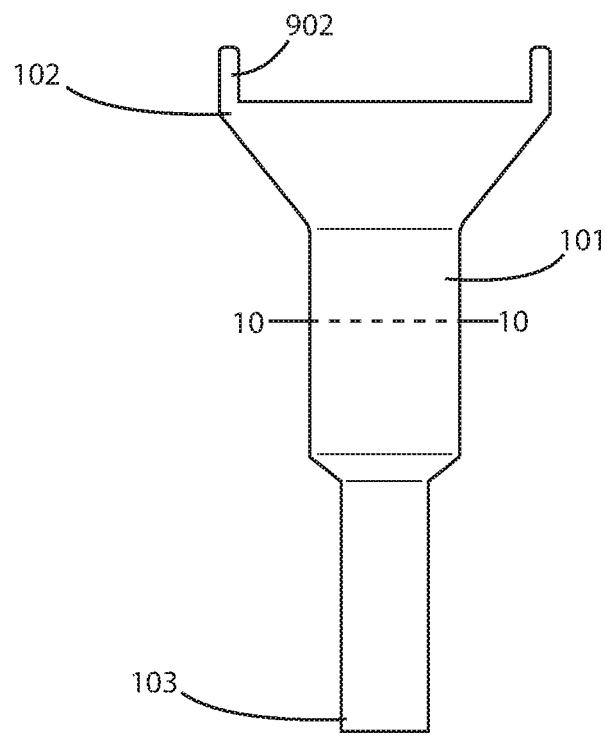
FIG. 9 is a schematic view of a guide sheath of an insertion tool in accordance with various embodiments herein.

In some embodiments, separation assist members or tabs can be mounted on the guide sheath and/or the protection tube in order to provide a user with a gripping point and/or leverage in order to assist in breaking the component into discrete portions. Referring now to FIG. 9, a schematic view of a guide sheath 101 is shown in accordance with various embodiments herein. The guide sheath 101 has a proximal end 102 and a distal end 103. Separation assist members 902 are disposed on the proximal end 102 of the guide sheath 101.

Figure 10:
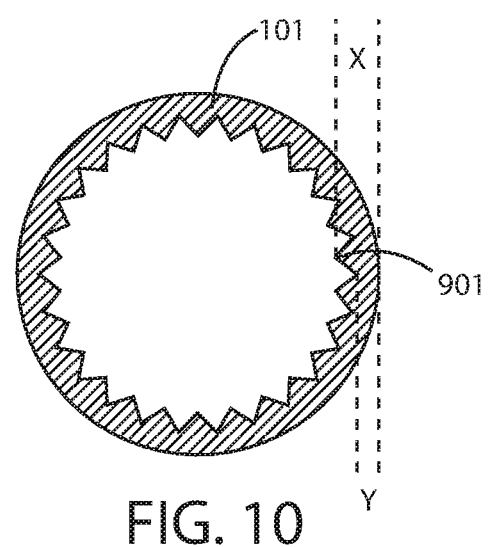
FIG. 10 is a schematic cross-sectional view of a portion of a guide sheath in accordance with various embodiments herein.

Referring now to FIG. 10, a cross-sectional view of the guide sheath 101 as taken along line 10-10 of FIG. 9 is shown. The inner surface of the guide sheath 101 comprises a plurality of ridges 901 running parallel to the lengthwise axis of the guide sheath 101 and about the circumference of the inner wall. The ridges 901 define areas of the wall having a first thickness (X), and between the ridges areas of the wall having a second thickness (Y) wherein the first thickness is greater than the second thickness. Material of guide sheath including a tubular member is configured to fracture along the length of the wall between the ridges when outward forces are applied to each half the tubular member. Also at the proximal end of the tubular member, a first notch or cut-out can be positioned adjacent to the proximal end of a first area of the of the tubular member that is between a first set of two ridges, and a second notch or cut-out can be positioned that is adjacent to the proximal end of a second area of the of the tubular member that is between a second set of two ridges. The guide sheath can also include first and second separation-assist members (such as 902 in FIG. 9) or tabs connected to the proximal end of the tubular member and opposite one another on the tubular member and between the first and second notches.

In some examples, various access device configurations may be provided with protection sleeves in various lengths to accommodate various catheter lengths. In some examples, the length of the protection sleeve can be variable, through adjustment of parts, or through selection of components of particular lengths. In some examples, access devices can be provided with a variety of stroke lengths, i.e. the length over which the movable section can move, and thus the distance that the distal end of the hemodialysis catheter can move, can be varied to suit a particular application. In some applications, the stroke length of an access device can be variable, for example by adjustment of mechanical stops.

In some examples, an insertion tool can be removable and replaceable, in the event that an original catheter becomes obstructed or otherwise compromised.

While various examples are described in the context of a insertion tools, an access device could be used with an indwelling catheter in other scenarios, such as central venous access for numerous reasons including: chemotherapy, parenteral nutrition, saline and fluid delivery, drug delivery, antibiotic delivery, frequent blood draws, blood stem cell collection, plasmapheresis, and monitoring of central venous pressure. Venous access can be either through tunneled or non-tunneled catheters and can be directly into central veins such as the subclavian or jugular veins or inserted into peripheral veins using a longer catheter to provide central access called a peripherally inserted central catheter (PICC) line.

As described above with regard to FIG. 7, portions of the insertion tool 100 can be covered with a coating. For example, hydrophilic polymeric coatings can be applied to portions of the medical device to impart lubricity and decrease particulate shedding. In some examples, portions of the distal end of the protection tube can be coated with hydrophilic polymers to induce lubricity. In other examples, the inner diameter of the insertion tool is coated or lined with lubricious low friction coatings or the outer diameter is lined with lubricious low friction coatings, friction reducing or lubricating materials such as silicone oil, perfluorinated oils or waxes or with covalently bonded coatings that imparts lower friction, such as hydrophilic polymers described herein.

Exemplary embodiments of surfaces, including low-friction surfaces for the devices herein include substrates prepared from low friction materials (e.g. PTFE and PTFE liners) and surfaces that can be made to be low friction by addition of coatings (e.g. coatings with hydrophilic polymers).

One class of hydrophilic polymers useful as polymeric materials for hydrophilic coating formation can be synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference. Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl) methacrylamide-co-N-[3-(4-benzoylbenzamido)propyl]

methacrylamide (Formula III). The preparation of the polymer is disclosed in Example 1 of US Patent Publication 2007/0032882 (to Lodhi, et al.), the full content of which is incorporated herein by reference.

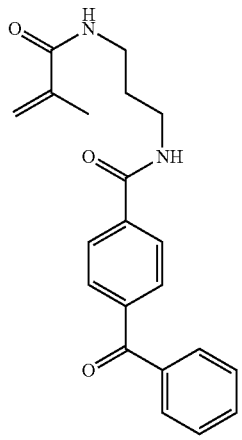

Formula I

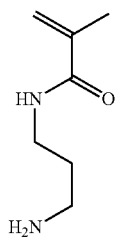

Formula II

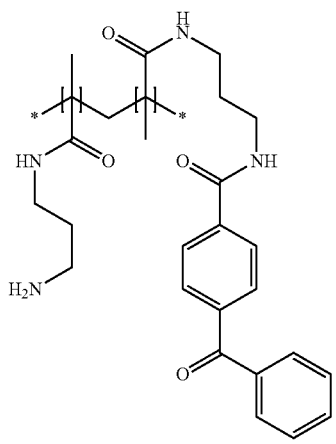

Formula III

In some embodiments, the hydrophilic polymer can be a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacylamide), "Photo PA", and derivatives thereof can be used to form hydrophilic coatings in exemplary embodiments of the present disclosure. Methods for the preparation of photo-polyacrylamide are described in U.S. Pat. No. 6,007,833, the disclosure of which is incorporated herein by reference.

Other embodiments of hydrophilic coatings include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic coatings that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic coating can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl)methacrylamide)-co-methoxy poly(ethylene glycol) monomethacrylate. Other negatively charged species that can be incorporated into the hydrophilic coating are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic coating are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photocrosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivatable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

(a)

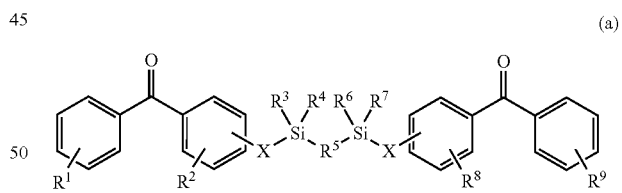

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)

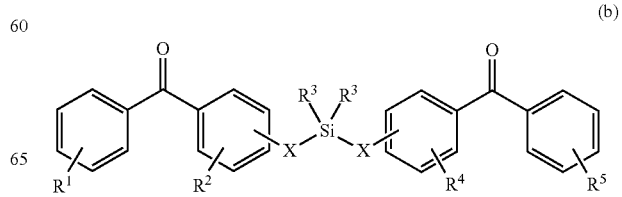

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)

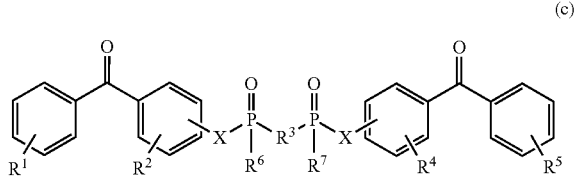

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)

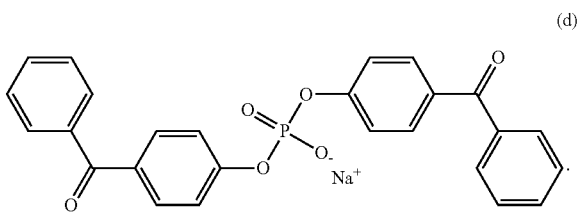

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y-X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis(4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

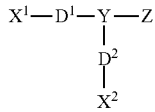

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

PG2-LE2-X-LE1-PG1 wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference. Further embodiments of non-ionic photoactivatable crosslinking agents can include, for example, those described in US Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula R1-X-R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which are herein incorporated by reference.

In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

(I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B-R1, B-R2 and B-R3 can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic coating. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used between the hydrophilic layer and the substrate. In yet other instances the tie layer can be added to the hydrophilic layer. The tie layer can act to increase the adhesion of the hydrophilic layer to the substrate. In other embodiments, the tie layer can act to increase adhesion of the hydrophobic active agent to the hydrophilic layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic layer can include tannic acid, polydopamine or other catechol containing materials.

In various embodiments, methods are included herein. In an embodiment, a method for inserting a medical device into a second medical device, such as a hemostasis sealing valve, is included. The method can include aligning an insertion tool with a hemostasis sealing valve. The insertion tool can include a guide sheath and a protection tube. The guide sheath can include a proximal end and a distal end, the proximal end being flared. The guide sheath can further include an inner surface defining a central lumen, the guide sheath can further include a locking notch disposed on the inner surface between the proximal end and the distal end. The protection tube can include a proximal end and a distal end, the proximal ended being flared. A portion of the protection tube can be situated within the central lumen of the guide sheath. The flared proximal end of the protection tube can be sized to fit within the locking notch and can have an outer diameter larger than portions of the inner surface immediately adjacent to the locking notch. The method can further include inserting the distal end of the protection tube into the hemostasis sealing valve. The method can further include inserting the medical device through the central lumen of the guide sheath into the protection tube and through the hemostasis sealing valve. The method can further include separating the guide sheath into discrete portions. The method can further include separating the protection tube into discrete portions. The method can further include inserting the protection tube into the guide sheath until the flared proximal end of the protection tube engages the locking notch.

Figure 11:
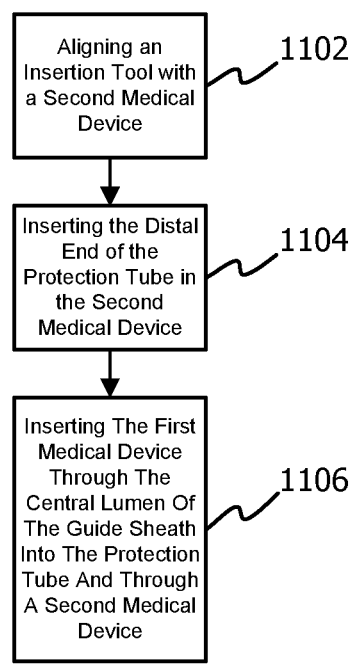
FIG. 11 is a flowchart of a method in accordance with various embodiments herein.

Referring now to FIG. 11, a flowchart of an exemplary method is shown. The method can include aligning 1102 an insertion tool with a second medical device (such as a hemostasis sealing valve). The method can further include inserting 1104 the distal end of the protection tube into the second medical device. The method can further include inserting 1106 the first medical device through the central lumen of the guide sheath into the protection tube and through a second medical device.

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

Aspects have been described with reference to various specific and preferred embodiments and techniques. However, it should be understood that many variations and modifications may be made while remaining within the spirit and scope herein.

The invention claimed is:

1. An insertion tool comprising:
   (i) a guide sheath comprising a proximal end and a distal end, the guide sheath being flared on the proximal end and tapering to an opening on the distal end, the guide sheath comprising an inner surface defining a central lumen, the guide sheath further comprising a locking notch disposed on the inner surface between the proximal end and the distal end; and
   (ii) a protection tube comprising a proximal end and a distal end, the proximal end of the protection tube comprising a locking flare;
   wherein the locking flare at the proximal end of the protection tube is situated within the central lumen of the guide sheath; and
   wherein the locking flare at the proximal end of the protection tube is sized to fit within the locking notch of the guide sheath and has an outer diameter larger than portions of the inner surface of the guide sheath immediately adjacent to the locking notch; and
   wherein the distal end of the protection tube extends beyond the distal end of the guide sheath by a distance of 2 mm to 10 mm when the proximal end of the protection tube is seated within the locking notch of the guide sheath.

2. The insertion tool of claim 1, the inner surface of the guide sheath comprising a plurality of ridges oriented parallel to a lengthwise axis of the guide sheath.

3. The insertion tool of claim 1, the inner surface of the guide sheath comprising a plurality of projections oriented parallel to a lengthwise axis of the guide sheath.

4. The insertion tool of claim 1, an inner surface of the protection tube comprising a plurality of ridges oriented parallel to a lengthwise axis of the protection tube.

5. The insertion tool of claim 1, an inner surface of the protection tube comprising a plurality of projections oriented parallel to a lengthwise axis of the protection tube.

6. The insertion tool of claim 1, the distal end of the protection tube comprising a tapered portion.

7. The insertion tool of claim 1, the locking flare at the proximal end of the protection tube having an outside average diameter of about 0.75 mm to about 12 mm.

8. The insertion tool of claim 1, wherein the distance between the distal end of the guide sheath and the distal end of the protection tube is about 2 mm to about 10 mm when the locking flare at the proximal end of the protection tube is situated within the locking notch.

9. The insertion tool of claim 1, the protection tube comprising an inner surface defining a central lumen.

10. The insertion tool of claim 1, the guide sheath comprising a polymer.

11. The insertion tool of claim 10, the polymer selected from the group consisting of polyamide, polyimide, polyether block amide (PEBAX), polyether ether ketone (PEEK), high density polyethylene (HDPE), polyethylene, polyurethane, or polyethylene vinyl acetate.

12. The insertion tool of claim 1, the protection tube comprising a polymer.

13. The insertion tool of claim 12, the polymer selected from the group consisting of polyamide, polyimide, polyether block amide (PEBAX), polyether ether ketone (PEEK), high density polyethylene (HDPE), polyethylene, polyurethane, or polyethylene vinyl acetate.

14. The insertion tool of claim 1, the guide sheath comprising a wall thickness that is thicker than a wall thickness of the protection tube.

15. The insertion tool of claim 1, further comprising a hydrophilic coating disposed on the inner surface of the guide sheath.

16. The insertion tool of claim 1, further comprising a hydrophilic coating disposed on the inner surface of the protection tube.

17. The insertion tool of claim 1, the guide sheath wall comprising a weakened separation line to facilitate separating the guide sheath into distinct segments.

18. The insertion tool of claim 1, the protection tube wall comprising a weakened separation line to facilitate separating the protection tube into distinct segments.

19. An insertion tool comprising:
   (i) a guide sheath having an outer diameter, an inner diameter, a proximal end and a distal end, the guide sheath being flared on the proximal end and tapering to an opening on the distal end, and a locking notch disposed on an inner surface of the guide sheath between the proximal end and the distal end; and
   (ii) a protection tube having an outer diameter, an inner diameter, a locking flare disposed at a proximal end and a tapered distal end;
   wherein the protection tube outer diameter is less than the guide sheath inner diameter and the locking flare at the proximal end of the protection tube is situated within the guide sheath; and
   wherein the locking flare at the proximal end of the protection tube is sized to fit within the locking notch of the guide sheath; and
   wherein the distal end of the protection tube extends beyond the distal end of the guide sheath by a distance of 2 mm to 10 mm when the proximal end of the protection tube is seated within the locking notch of the guide sheath.

20. A method for inserting a first medical device into a second medical device comprising:
   aligning an insertion tool with the second medical device, the insertion tool comprising:
      (i) a guide sheath comprising a proximal end and a distal end, the guide sheath being flared on the proximal end and tapering to an opening on the distal end, the guide sheath comprising an inner surface defining a central lumen, the guide sheath further comprising a locking notch disposed on the inner surface between the proximal end and the distal end; and
      (ii) a protection tube comprising a proximal end and a distal end, the proximal end of the protection tube comprising a locking flare;
      wherein the locking flare at the proximal end of the protection tube is sized to fit within the locking notch of the guide sheath and has an outer diameter larger than portions of the inner surface of the guide sheath immediately adjacent to the locking notch; and
      wherein the distal end of the protection tube extends beyond the distal end of the guide sheath by a distance of 2 mm to 10 mm when the proximal end of the protection tube is seated within the locking notch of the guide sheath;
   inserting the distal end of the protection tube into the second medical device; and
   inserting the first medical device through the central lumen of the guide sheath into the protection tube and through the second medical device.

21. The method of claim 20, further comprising inserting the protection tube into the guide sheath until the locking flare at the proximal end of the protection tube engages the locking notch of the guide sheath.

* * * * *